United States Patent
Diekmann et al.

(10) Patent No.: US 7,477,395 B2
(45) Date of Patent: Jan. 13, 2009

(54) MEASURING DEVICE

(75) Inventors: Wilfried Diekmann, Luebeck (DE); Lars Wulf, Sereetz (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 22 days.

(21) Appl. No.: 11/764,430

(22) Filed: Jun. 18, 2007

(65) Prior Publication Data
US 2008/0106741 A1  May 8, 2008

(30) Foreign Application Priority Data
Aug. 16, 2006  (DE) .............. 10 2006 038 365

(51) Int. Cl.
G01N 21/00 (2006.01)
G01N 21/35 (2006.01)
G01J 5/02 (2006.01)

(52) U.S. Cl. ............... 356/437; 250/431.3; 250/431.5; 250/343; 250/338.5

(58) Field of Classification Search ......... 356/432–448, 356/246, 244; 250/343, 341.5, 336.1, 338.5, 250/353, 349, 341.3; 73/25.01, 24.02, 24.03; 359/639
See application file for complete search history.

(56) References Cited

U.S. PATENT DOCUMENTS

| | | | | |
|---|---|---|---|---|
| 4,383,181 A * | 5/1983 | Roess et al. | ................. | 250/573 |
| 5,559,333 A * | 9/1996 | Araya et al. | ................. | 250/344 |
| 5,874,737 A * | 2/1999 | Bytyn et al. | ................. | 250/343 |
| 5,886,348 A | 3/1999 | Lessure et al. | | |
| 5,923,035 A | 7/1999 | Winkler et al. | | |
| 6,150,661 A * | 11/2000 | McCaul et al. | ............... | 250/343 |
| 6,665,124 B2 * | 12/2003 | Weckstrom | ................. | 359/639 |
| 6,843,102 B1 * | 1/2005 | Shulga et al. | ............... | 73/25.01 |
| 6,989,549 B2 * | 1/2006 | Diekmann et al. | ........... | 250/573 |
| 7,259,374 B2 * | 8/2007 | Wong | ................... | 250/339.13 |

FOREIGN PATENT DOCUMENTS

| | | |
|---|---|---|
| DE | 197 13 928 C1 | 4/1998 |
| DE | WO 2004/097381 | 11/2004 |
| WO | WO 96/01418 | 1/1996 |

\* cited by examiner

*Primary Examiner*—Sang Nguyen
(74) *Attorney, Agent, or Firm*—McGlew & Tuttle, P.C.

(57) ABSTRACT

A measuring device for determining the concentrations of gases by radiation absorption. The device includes at least one radiation source for generating radiation, a measuring cell, which is arranged downstream of the radiation source and in which the medium to be measured is located and at least one radiation detector, which is reached by the radiation after it has been sent through the measuring cell. A radiation guide device is provided by which the radiation is guided to the radiation detector. The radiation guide device includes a main optical unit, which has, on the one hand, an optical element (4), so that the punctiform radiation source is imaged in a bar-shaped radiation spot (5) extending along a preferred direction (1), and which has, on the other hand, parallel reflection surfaces (7, 7'), which extend at right angles to the preferred direction and at the inner surfaces of which the radiation is totally reflected between the optical element (4) and the radiation detector (3, 3').

20 Claims, 5 Drawing Sheets

MEASURING DEVICE

CROSS REFERENCE TO RELATED APPLICATIONS

This application claims the benefit of priority under 35 U.S.C. § 119 of German Patent Application DE 10 2006 038 365.6 filed Aug. 16, 2006, the entire contents of which are incorporated herein by reference.

FIELD OF THE INVENTION

The present invention pertains to a measuring device for determining the concentrations of gases by radiation absorption with at least one radiation source for generating radiation, with a measuring cell, which is arranged downstream of the radiation source in the direction of the radiation and in which the medium to be measured is located, with at least one radiation detector, which the radiation reaches after it has been passed through the measuring cell, and with a radiation guide means, by means of which the radiation is guided to the radiation detector.

BACKGROUND OF THE INVENTION

A measuring device for determining the concentrations of gases by infrared absorption, which has two radiation sources and two radiation detectors, is known from DE 197 13 928 C1. A first radiation detector is used as a measuring detector and a second radiation detector as a reference detector. The wavelength range of the radiation detector is coordinated with the absorption of the radiation by the substance, whose concentration is to be measured. The reference detector measures the radiation in a range that is not affected by this substance. The reference signal provided by the reference detector is used to compensate variations of the incident radiation capacity.

To obtain a good measurement result, it is desirable that the radiation guide means of the measuring device is designed such that the radiation detector is reached by the highest radiation intensity possible, so that a high signal-to-noise ratio can be obtained. The radiation guide means may have means for this purpose, to ensure that the radiation is focused to the radiation detector. However, sharp imaging of the radiation on the detector has the drawback that the accuracy of the measurement result depends very strongly on the adjustment of the radiation guide means. To avoid the undesired effects of maladjustment, provisions may be made for producing an enlargement of the radiation spot in an area in front of or behind the radiation detector by focusing the radiation. However, undesired shadowing of the radiation, which may lead to considerable errors of measurement, are associated with such a "defocusing."

Non-imaging concentrators are arranged in front of the radiation detectors in the device known from DE 197 13 928 C1. These shall bundle the radiation incident in parallel and generate a uniform radiation distribution in the plane of the radiation detectors. However, the drawback is that a shift of the intensity distribution takes place in case of maladjustment, and different intensity reductions generate varying signal ratios, which in turn lead to a drift.

SUMMARY OF THE INVENTION

The object of the present invention is to perfect a measuring device for determining the concentrations of gases such that drifts as a consequence of shadowing or mechanical maladjustment are further reduced.

According to the invention, a measuring device is provided for determining the concentrations of gases by radiation absorption. The measuring device includes a radiation source for generating radiation, a measuring cell arranged downstream of the radiation source in the direction of emitted radiation, the medium to be measured being located in the measuring cell a radiation detector disposed in a position reached by the radiation after having passed through the measuring cell and a radiation guide means by which the radiation is guided to the radiation detector. The radiation guide means comprises a main optical unit, which has, on the one hand, an optical element, so that the punctiform radiation source is imaged in a bar-shaped radiation spot extending along a preferred direction, and which has, on the other hand, parallel reflection surfaces extending at right angles to the preferred direction, on the inner surfaces of which the radiation is totally reflected between the optical element and the radiation detector.

According to the present invention, the combination of an optical element and parallel reflection surfaces of a main optical unit, which the reflection surfaces are associated with same, make it possible for the entire radiation intensity to be distributed uniformly on the radiation detector, the optical element being designed such that a bar-shaped radiation spot is generated on the radiation detector.

The optical element of the main optical unit is designed such that the radiation source or an intermediate image thereof is imaged sharply on the radiation detector at right angles to the preferred direction. Shadowing therefore leads to a uniform reduction of the radiation intensity over the width of the bar-shaped radiation spot. In a second plane in the preferred direction, along the bar-shaped radiation spot, the course of the shadow is distributed on the outlet area corresponding to the number of reflections on the parallel reflection surfaces such that the contrast of the shadow becomes low. The strong effect of shadowing on the accuracy of measurement advantageously decreases in this manner.

According to a preferred embodiment of the present invention, the optical element of the main optical unit is circular or elliptical in a plane of curvature of the main optical unit, so that focusing is guaranteed in the preferred direction of the radiation detector. The preferred direction, along which the radiation detector extends, extends at right angles to the plane of curvature.

According to a variant of the present invention, the optical element of the main optical unit has depressions. The flank angle of the depression should be smaller than half the opening angle of the field of detection of the radiation detector in order to avoid losses of intensity.

According to a variant of the present invention, a foreoptical unit, which makes radiation available to the main optical unit with relatively high radiation intensity and a relatively great divergence angle, is formed in front of the main optical unit in the direction of radiation.

Exemplary embodiments of the present invention will be explained in more detail below on the basis of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENT

The measuring device according to the present invention can be used to determine the concentration of a component of a gas mixture as a medium to be measured, an absorption spectrum of a radiation in the visible or ultraviolet or infrared wavelength range being imposed to the gas.

Figure 1:
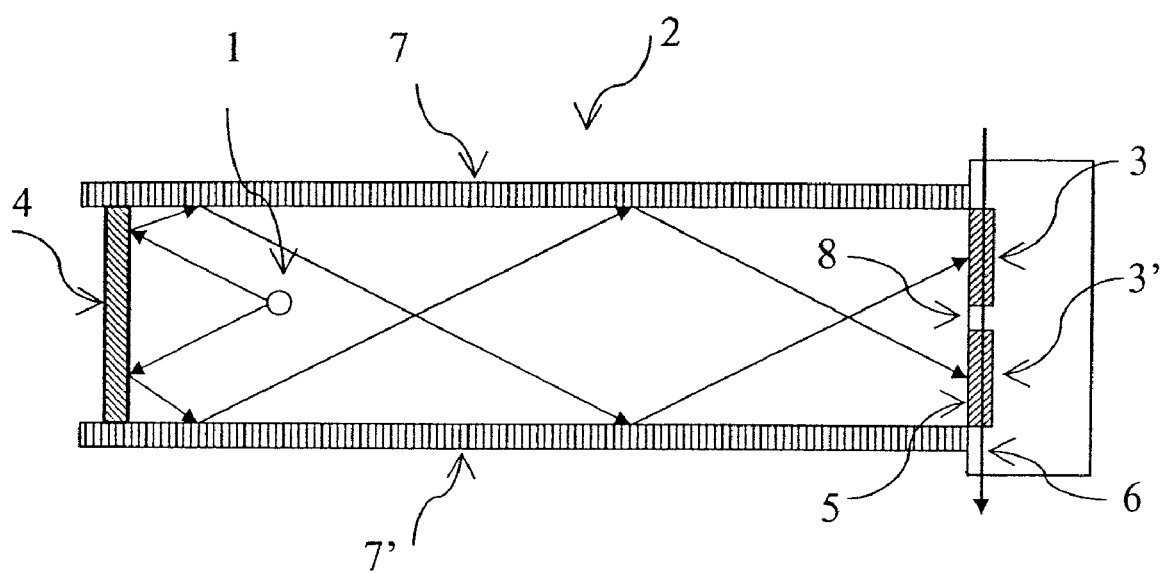
FIG. 1 is a schematic longitudinal sectional view through an exemplary measuring device.

Referring to the drawings in particular, FIG. 1 shows an example of the design of the measuring device. The measuring device comprises a radiation source 1, a radiation guide means with a main optical unit 2 as well as two radiation detectors 3, 3'. The medium (gas) to be measured is arranged within the encapsulated measuring device. The main optical unit 2 has a cylindrical optical element 4 in the form of a cylinder mirror, which images the punctiform radiation source 1 in a bar-shaped radiation spot 5, which extends in a focal plane of the optical element 4, which plane is identical to the plane in which the radiation detectors 3, 3' extend, along a preferred direction 6. To avoid errors of measurement, the main optical unit 2 has two parallel reflection surfaces 7, 7', which extend continuously between the optical element 4 and the radiation detectors 3, 3'. The reflection surfaces 7, 7' extend a distance to a location corresponding to the length of the radiation detectors 3, 3', so that the radiation losses are limited to the intermediate space 8 between the radiation detectors 3, 3'.

Figure 2:
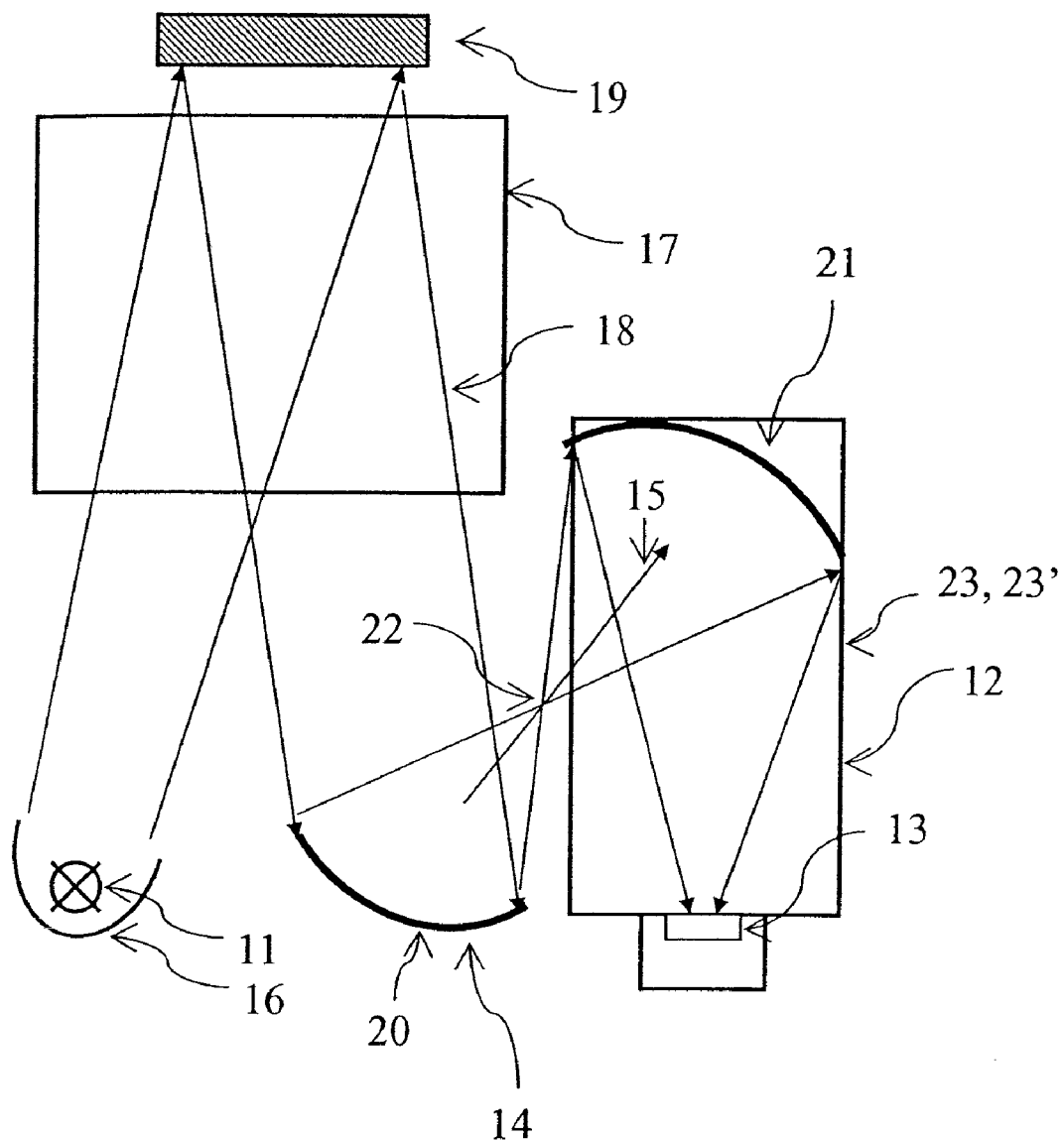
FIG. 2 is a schematic longitudinal sectional view through a measuring device according to a first embodiment.

A measuring device according to FIG. 2 has a radiation source 11, a main optical unit 12, a radiation detector 13 as well as a foreoptical unit 14. The foreoptical unit 14 is arranged in front of the main optical unit 12 in the direction of radiation 15. The radiation guide means is formed essentially by the main optical unit 12 and the foreoptical unit 14.

A parabolic reflector 16 collimates the radiation in the direction of a measuring cell 17 (measuring section). The parabolic reflector 16 is associated with the radiation source 11. The radiation bundle 18 (radiation) is guided over a tilted (angled relative to the location of the source 11) mirror 19 in the direction of the foreoptical unit 14. As an alternative, the foreoptical unit 14 and the main optical unit 12 may also be arranged in a mirrored pattern on a side of the measuring cell 17 located opposite the radiation source 11, while the tilted mirror 19 is eliminated.

The foreoptical unit 14 has essentially a paraboloid reflector 20, which has a relatively short focal length, so that a radiation cone with a relatively large dihedral angle is generated. The paraboloid reflector 20 is designed such that the dihedral angle of the image of the radiation source is adapted to the detection field of the radiation detector 13.

The main optical unit 12 has an elliptical reflector 21, which has a first focal point at the site of the intermediate image 22 of the light source and a second focal point in the plane in which the radiation detector 13 extends.

The radiation bundle 18 is reflected in the direction of the radiation detector 13 by means of the optical element designed as an ellipsoidal reflector 21, the radiation 18 being totally reflected on the opposite parallel, flat reflection surfaces 23, 23' of the main optical unit 12. As is apparent from FIG. 2, the reflector 21 extends elliptically in a plane of curvature, which extends at right angles to the preferred direction 6. The flat reflection surfaces 23, 23' extend in parallel to the plane of curvature of the reflector 21 and at right angles to the preferred direction 6. Compared to FIG. 1, the reflection surfaces 23, 23' are rotated by 90° and are located one on top of another in FIG. 2. The preferred direction, not shown more specifically, extends at right angles to the drawing plane.

Figure 3A:
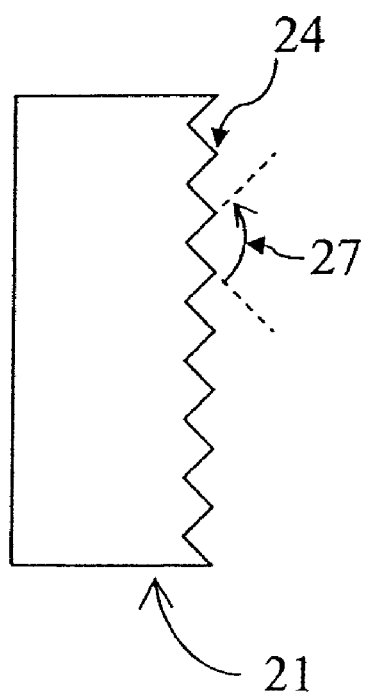
FIG. 3a is a sectional view through an optical element of a main optical unit of the measuring device with a prismatic contour.
Figure 3B:
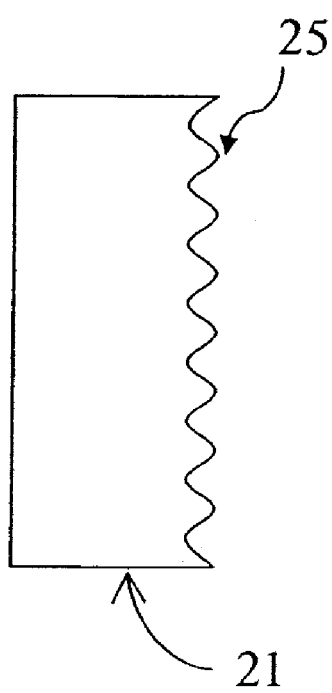
FIG. 3b is a sectional view through an optical element of a main optical unit of the measuring device with a wave-shaped contour.
Figure 3C:
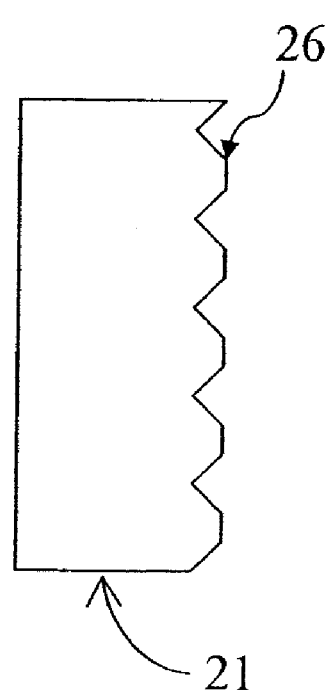
FIG. 3c is a sectional view through an optical element of a main optical unit of the measuring device with a dome-shaped contour.

As an alternative, the elliptical reflector 21 may also be of a cylindrical design. The reflector 21 of the main optical unit 12 may have, as is shown in FIG. 3a, prismatic depressions 24, which extend at right angles to the preferred direction 6. As an alternative, the optical element may also have wave-shaped depressions 25 or dome-shaped depressions 26. A flank angle 27 of the depression 24 should be smaller than half the opening angle of the detection field of the radiation detector 13 in order to avoid intensity losses.

Figure 4:
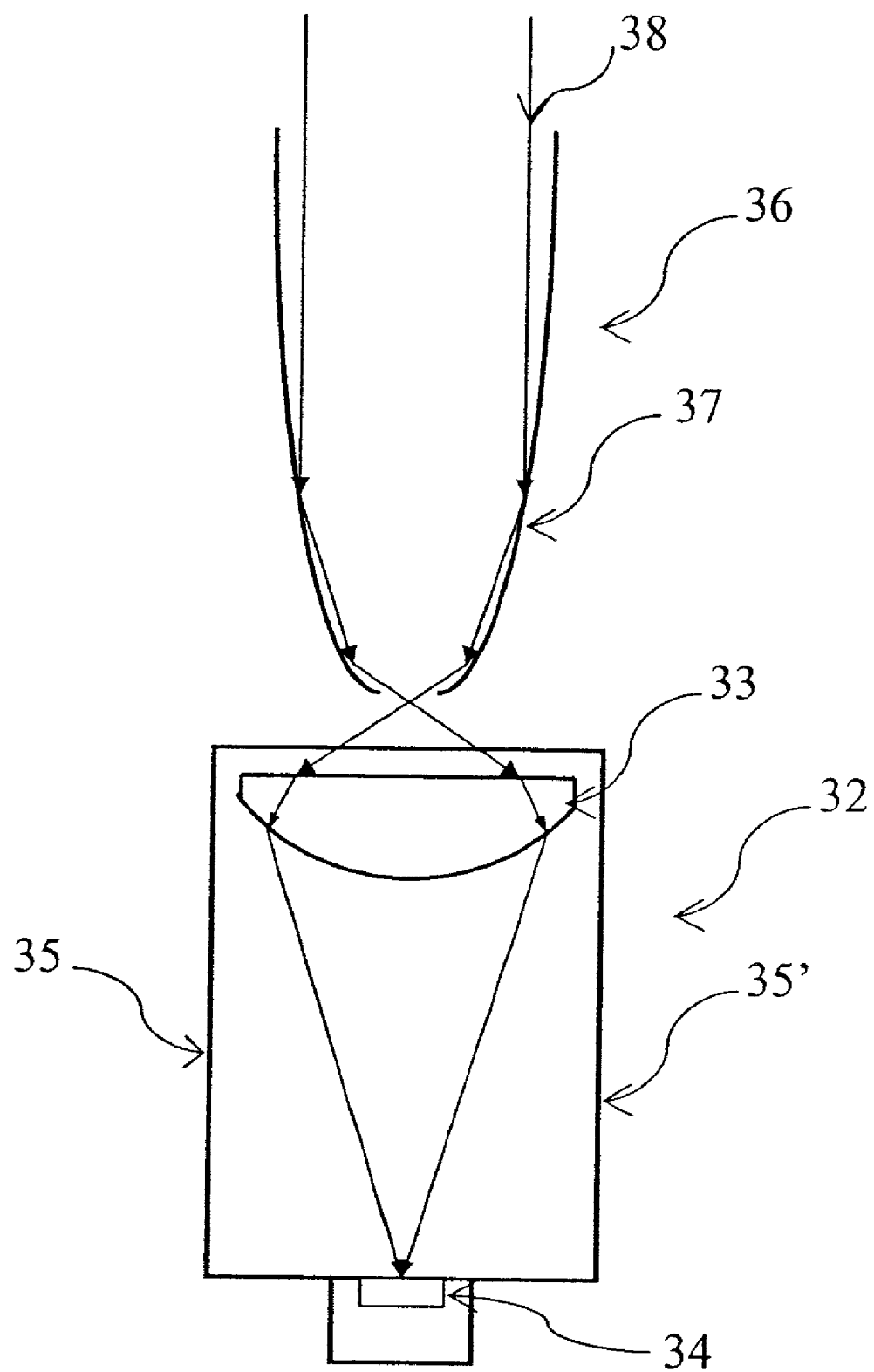
FIG. 4 is a schematic longitudinal sectional view through a foreoptical and main optical unit of a measuring device according to a second embodiment.

According to another embodiment of a measuring device according to FIG. 4, a main optical unit 32 may have a cylindrical lens 33 as the optical element. The parallel, flat reflection surfaces 35 extend between the optical element 33 and a radiation detector 34. A foreoptical unit 36 is formed essentially by an optical concentrator 37, which is designed as a concentrator tapering in the direction of radiation. The concentrator 37 makes possible the bundling of a radiation 38, which is present as a parallel radiation on the inlet side, so that the greatly divergent radiation bundle 38 is focused by means of the cylindrical optical element 33 onto the radiation detector 34.

Figure 5:
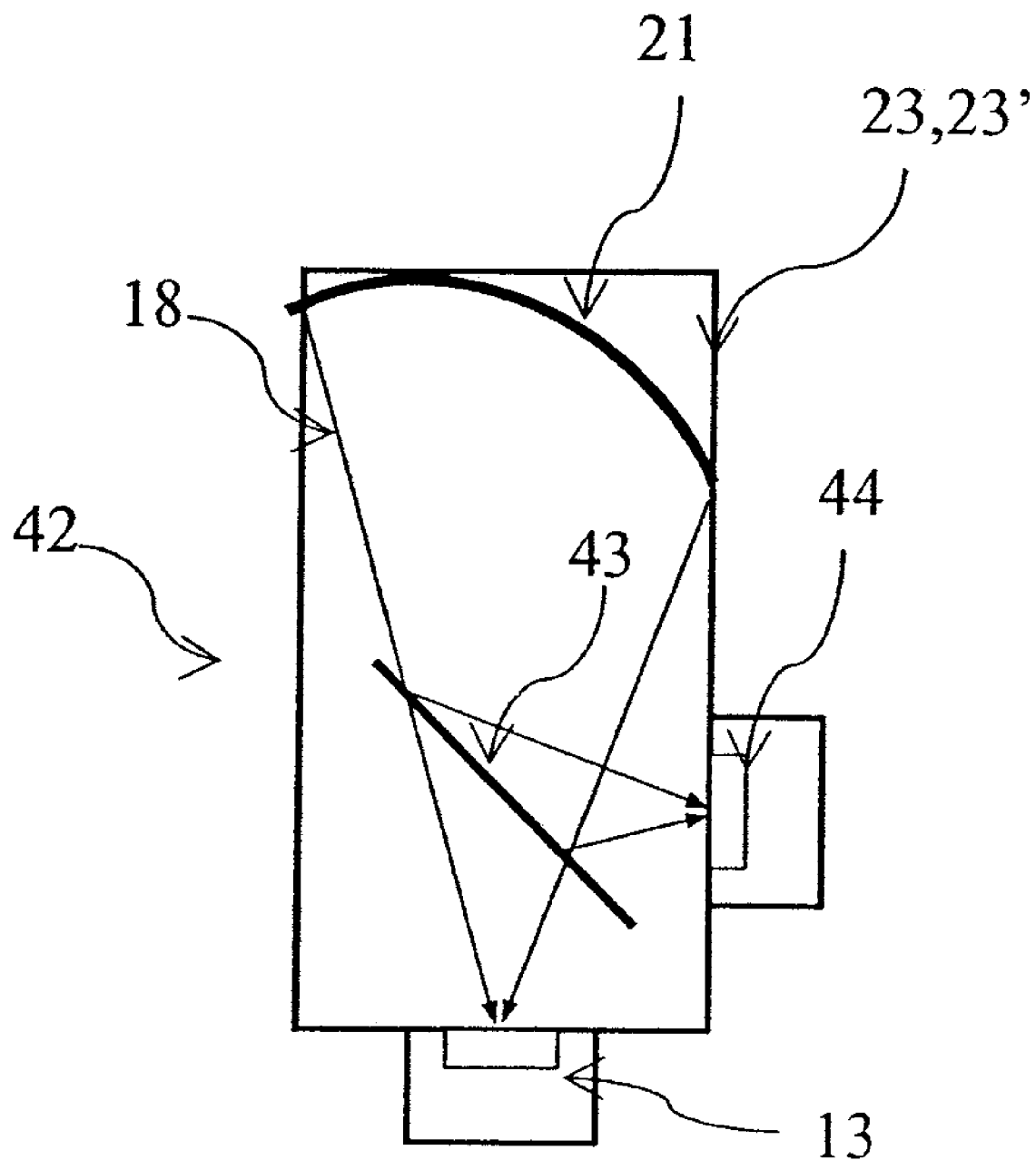
FIG. 5 is a longitudinal sectional view through a main optical unit according to another embodiment containing a beam splitter and two radiation detectors arranged at an angle relative to one another.

According to an embodiment of a main optical unit 42 according to FIG. 5, which is an alternative to the embodiment according to FIG. 2, the main optical unit 42 may comprise a beam splitter 43, so that part of the radiation bundle falls on the radiation detector 13 and another part of the radiation bundle on another radiation detector 44 arranged on the side. The beam splitter 43 is arranged at an angle of 45° to an axis along the direction of propagation of the light. The main optical unit 42 is limited by the parallel reflection surfaces 23, 23'. Identical components and component functions are designated with the same reference numbers.

A plurality of radiation detectors 13, 44 can be advantageously used for the measurement as a result. The additional radiation detector 44 may optionally also be used in a different wavelength range. The additional radiation detector 44 is preferably located on a side of the main optical unit 42 facing away from the foreoptical unit 14 (FIG. 2).

The radiation detectors 13, 34, 44 are preferably designed as double radiation detectors, which are arranged in rows each at right angles to the plane of the sheet. The optical elements of the main optical unit may be designed as lenses, as parabolic reflectors or elliptical reflectors.

The main optical unit may have a rectangular cross section, the walls being formed by opposite reflection surfaces 23, 23', 35, 35'.

While specific embodiments of the invention have been shown and described in detail to illustrate the application of the principles of the invention, it will be understood that the invention may be embodied otherwise without departing from such principles.

What is claimed is:

1. A measuring device for determining the concentrations of gases by radiation absorption, the measuring device comprising:
   a radiation source for generating radiation;
   a measuring cell arranged downstream of said radiation source in a direction of emitted radiation, a medium to be measured being located in said measuring cell;
   a radiation detector disposed in a position reached by said radiation after having passed through said measuring cell; and
   a radiation guide means, by means of which the radiation is guided to the radiation detector, said radiation guide means comprising a main optical unit including an optical element for imaging a punctiform radiation source in a bar-shaped radiation spot extending along a preferred direction and including parallel reflection surfaces extending at right angles to said preferred direction including inner surfaces which totally reflect said radiation between said optical element and said radiation detector.

2. A measuring device in accordance with claim 1, wherein said optical element of said main optical unit extends circularly or elliptically in a plane of curvature, said preferred direction, along which said radiation detector extends being at right angles to said plane of curvature.

3. A measuring device in accordance with claim 1, wherein said optical element of said main optical unit has a contour with depressions extending at right angles to said preferred direction.

4. A measuring device in accordance with claim 3, wherein each depression of said depressions has a flank angle that is smaller than half an opening angle of a field of detection of said radiation detector.

5. A measuring device in accordance with claim 1, wherein said parallel reflection surfaces are flat and extend from a plane in which said optical element extends to a plane in which said radiation detector extends.

6. A measuring device in accordance with claim 1, wherein said radiation guide means has a foreoptical unit arranged in front of said main optical unit with respect to a direction of radiation of said radiation source such that a dihedral angle of an image of said radiation source is adapted to a field of detection of said radiation detector.

7. A measuring device in accordance with claim 6, wherein said foreoptical unit comprises a paraboloid reflector arranged in a plane in which said radiation detector extends, such that radiation arriving from said measuring cell is guided in a direction of said optical element of said main optical unit.

8. A measuring device in accordance with claim 6, wherein said foreoptical unit comprises an optical concentrator.

9. A measuring device in accordance with claim 1, further comprising:
   a second radiation detector; and
   a beam splitter arranged between said parallel reflection surfaces such that a part of the radiation is deflected to said second radiation detector.

10. A measuring device in accordance with claim 1, wherein said radiation detector comprises a double radiation detector with elements arranged in a row-like pattern along said preferred direction.

11. A gas concentration measuring device, the measuring device comprising:
    a radiation source for emitting radiation directed in an emitted radiation direction;
    a measuring cell arranged spaced from said radiation source in said emitted radiation direction, gas to be measured being located in said measuring cell;
    a radiation detector for receiving emitted radiation after the emitted radiation has passed through said measuring cell; and
    a radiation guide means for guiding emitted radiation in a region between said radiation detector and said radiation source, said radiation guide means comprising a main optical unit including an optical element for imaging emitted radiation on a bar-shaped radiation region extending along a preferred direction and including parallel reflection surfaces extending at right angles to said preferred direction, said parallel reflection surfaces each totally reflecting radiation in a region between said optical element and said radiation detector.

12. A measuring device in accordance with claim 11, wherein said optical element has a circularly or elliptically extending portion with a plane of curvature, said preferred direction being at right angles to said plane of curvature.

13. A gas concentration measuring device in accordance with claim 11, wherein said optical element has a contour with depressions extending at right angles to said preferred direction.

14. A gas concentration measuring device in accordance with claim 13, wherein each depression of said depressions has a flank angle that is smaller than half an opening angle of a field of detection of said radiation detector.

15. A gas concentration measuring device in accordance with claim 11, wherein said parallel reflection surfaces are flat and extend from a plane in which said optical element extends to a plane in which said radiation detector extends.

16. A gas concentration measuring device in accordance with claim 11, wherein said radiation guide means has a foreoptical unit arranged in front of said main optical unit with respect to said emitted radiation direction such that a dihedral angle of an image of said radiation source is adapted to a field of detection of said radiation detector.

17. A gas concentration measuring device in accordance with claim 16, wherein said foreoptical unit comprises a paraboloid reflector arranged in a plane in which said radiation detector extends, such that radiation arriving from said measuring cell is guided in a direction of said optical element of said main optical unit.

18. A gas concentration measuring device in accordance with claim 11, wherein said foreoptical unit comprises an optical concentrator.

19. A gas concentration measuring device in accordance with claim 11, further comprising:
    a second radiation detector; and
    a beam splitter arranged between said parallel reflection surfaces such that a part of the radiation is deflected to said second radiation detector.

20. A gas concentration measuring device in accordance with claim 11, wherein said radiation detector comprises a double radiation detector with elements arranged in a row-like pattern along said preferred direction.

* * * * *